(12) United States Patent
van Geen et al.

(10) Patent No.: US 8,701,505 B2
(45) Date of Patent: Apr. 22, 2014

(54) PELTIER FREEZE-SHOE SAMPLER TO RECOVER AQUIFER SEDIMENT AND GROUNDWATER

(75) Inventors: Alexander van Geen, New York, NY (US); Benjamin Bostick, New York, NY (US); Christopher Manning, Troy, ID (US)

(73) Assignee: The Trustees of Columbia University in the City of New York, New York, NY (US)

( * ) Notice: Subject to any disclaimer, the term of this patent is extended or adjusted under 35 U.S.C. 154(b) by 84 days.

(21) Appl. No.: 13/210,854

(22) Filed: Aug. 16, 2011

(65) Prior Publication Data

US 2012/0167698 A1   Jul. 5, 2012

Related U.S. Application Data

(60) Provisional application No. 61/374,193, filed on Aug. 16, 2010.

(51) Int. Cl.
*G01N 1/10* (2006.01)
(52) U.S. Cl.
USPC ............. 73/863.11; 73/863.81; 73/864.33
(58) Field of Classification Search
USPC ............ 73/863, 863.11, 864, 864.31, 864.41, 73/864.44, 864.51, 864.53
See application file for complete search history.

(56) References Cited

U.S. PATENT DOCUMENTS

| | | | |
|---|---|---|---|
| 3,497,018 A * | 2/1970 | Gibson et al. ............... | 175/6 |
| 4,660,423 A | 4/1987 | Armstrong et al. | |
| 4,989,678 A * | 2/1991 | Thompson ................. | 175/20 |
| 5,494,119 A | 2/1996 | Tully | |
| 6,378,631 B1 * | 4/2002 | Aumann et al. ............ | 175/249 |
| 6,769,317 B1 * | 8/2004 | Hamilton et al. .......... | 73/864.44 |
| 7,140,264 B2 * | 11/2006 | Zeller ......................... | 73/863.11 |
| RE39,468 E * | 1/2007 | Ricker ........................ | 175/20 |
| 7,380,615 B1 * | 6/2008 | Vanearden ................. | 175/20 |
| 8,074,739 B2 * | 12/2011 | Sun et al. ................... | 175/17 |
| 2002/0134173 A1 * | 9/2002 | Lindgren et al. ........... | 73/863.11 |
| 2002/0194937 A1 * | 12/2002 | Scott et al. ................. | 73/864.91 |
| 2005/0016299 A1 * | 1/2005 | Zeller ......................... | 73/863.11 |
| 2009/0229382 A1 * | 9/2009 | Sun et al. ................... | 73/863.11 |
| 2010/0037712 A1 * | 2/2010 | Burton ....................... | 73/863.11 |
| 2010/0269599 A1 * | 10/2010 | Schroeter et al. .......... | 73/863.12 |

FOREIGN PATENT DOCUMENTS

WO   WO2006/089562   8/2006

OTHER PUBLICATIONS

Murphy et al., "A Sample-Freezing Drive Shoe for a Wireline-Piston Core Sampler", Ground Water Monitoring and Remediation, 1996, v. 16, No. 3. p. 86-90.*
Ahmed et al., "Ensuring safe drinking water in Bangladesh", *Science*, 314(5806): 1687-8 (Dec. 15, 2006).

* cited by examiner

Primary Examiner — David A Rogers
(74) Attorney, Agent, or Firm — Baker Botts LLP

(57) ABSTRACT

A groundwater sampling tool that includes an elongated hollow coring tube having a proximal end and a distal end for collecting groundwater and sediment; a Peltier element located in close proximity to a wall of the elongated hollow coring tube adapted to freeze groundwater and sediment collected by the elongated hollow coring tube.

18 Claims, 2 Drawing Sheets

PELTIER FREEZE-SHOE SAMPLER TO RECOVER AQUIFER SEDIMENT AND GROUNDWATER

The present application claims the benefit of U.S. Provisional Application No. 61/374,193, filed Aug. 16, 2010, and hereby incorporated by reference in its entirety.

BACKGROUND

Groundwater aquifers are a main source of drinking water for billions of people worldwide. There is, however, growing public concern about chronic exposure to natural, geogenic contaminants that can be released from uncontaminated sediment to groundwater. Natural constituents of groundwater recognized to be of significant health concern include fluoride and manganese. The metalloid arsenic (As) has received attention as a contaminant over the past two decades, particularly in south and southeast Asia. For example, elevated groundwater arsenic concentrations in many parts of Bangladesh has been described as the "largest poisoning of a population in history." Estimates of the rural population exposed to unsafe arsenic levels by drinking water in India, China, Myanmar, Pakistan Vietnam, Nepal and Cambodia has grown to over 100 million people.

Inappropriate sampling is one reason the multiple biogeochemical and hydrological factors contributing to the release of arsenic and other contaminants to groundwater have been difficult to isolate and fully understand, despite two decades of research by numerous international teams. Groundwater and aquifer solids are often collected separately by installing a well and coring to approximately the same depth, respectively. The high spatial variability within floodplain and delta deposits makes it therefore difficult to properly match solid phase and groundwater characteristics. Combining groundwater and sediment for incubation experiments can also create artifacts because of exposure of originally anoxic groundwater to atmospheric oxygen, contamination of the sediment with drilling fluid, and changing the in situ water/rock ratio. The mechanism of release and transport in groundwater of arsenic and other geogenic contaminants can hamper the ability to predict the fate of aquifer zones that can yield groundwater safe for human consumption. Nevertheless, such groundwater holds the greatest promise for reducing human exposure to natural contaminants in south and southeast Asia and other parts of the world in the foreseeable future.

Core catchers have been developed that attempt to minimize the loss of sediment upon retrieval, such devices can still result in the loss of sediment (e.g., sand) upon retrieval. Even when effective, core catchers also do not retain groundwater originally in contact with the sampled sediment interval.

Another approach to groundwater sample recovery is to seal the end of the coring tube, before retrieval, by freezing the contents with liquid $CO_2$ or $N_2$. See Murphy et al., A Sample-freezing Drive Shoe for a Wire Line Piston Core Sampler, Groundwater Monitoring Review, 16:86-90 (1996), which is hereby incorporated by reference. This approach can require a drill rig, sampling processing labs and liquid $CO_2$ or $N_2$ on hand at the field location.

Thus there remains a need for an efficient groundwater sampling tool to collect and process uncompromised aquifer samples, containing both sediment and groundwater, that can be easily implemented in the field and that does not require refrigerants like $CO_2$ or $N_2$. Such a tool would be useful for documenting and studying both natural and anthropogenic contamination of groundwater.

SUMMARY

Coring devices can be provided that employ Peltier coolers instead of $CO_2$ or $N_2$ refrigerants to create a frozen plug for retention of groundwater and sediment One aspect of the presently disclosed subject matter provides a groundwater sampling tool that includes an elongated hollow coring tube having a proximal end and a distal end for collecting groundwater and sediment, and a Peltier element located in close proximity to a wall of the elongated hollow coring tube adapted to freeze groundwater and sediment collected by the elongated hollow coring tube.

Another aspect of the presently disclosed subject matter provides a method of obtaining a groundwater sample that includes providing a groundwater sampling tool that includes an elongated hollow coring tube having a proximal end and a distal end for collecting groundwater and sediment, a Peltier element located in close proximity to a wall of the elongated hollow coring tube adapted to freeze groundwater and sediment contained within the elongated hollow coring tube, introducing the groundwater sampling tool to a subterranean source of groundwater and sediment, applying power from a power source to the elongated hollow coring tube for a time sufficient to freeze the sample of groundwater contained therein, and removing the groundwater sampling tool with the frozen sample of groundwater contained therein from the subterranean source of groundwater and sediment.

BRIEF DESCRIPTION OF THE DRAWINGS

The accompanying drawings, which are incorporated in and constitute part of this specification, are included to illustrate and provide a further understanding of the disclosed subject matter. Together with the description, the drawings serve to explain the principles of the disclosed subject matter.

DETAILED DESCRIPTION

Figure 1:
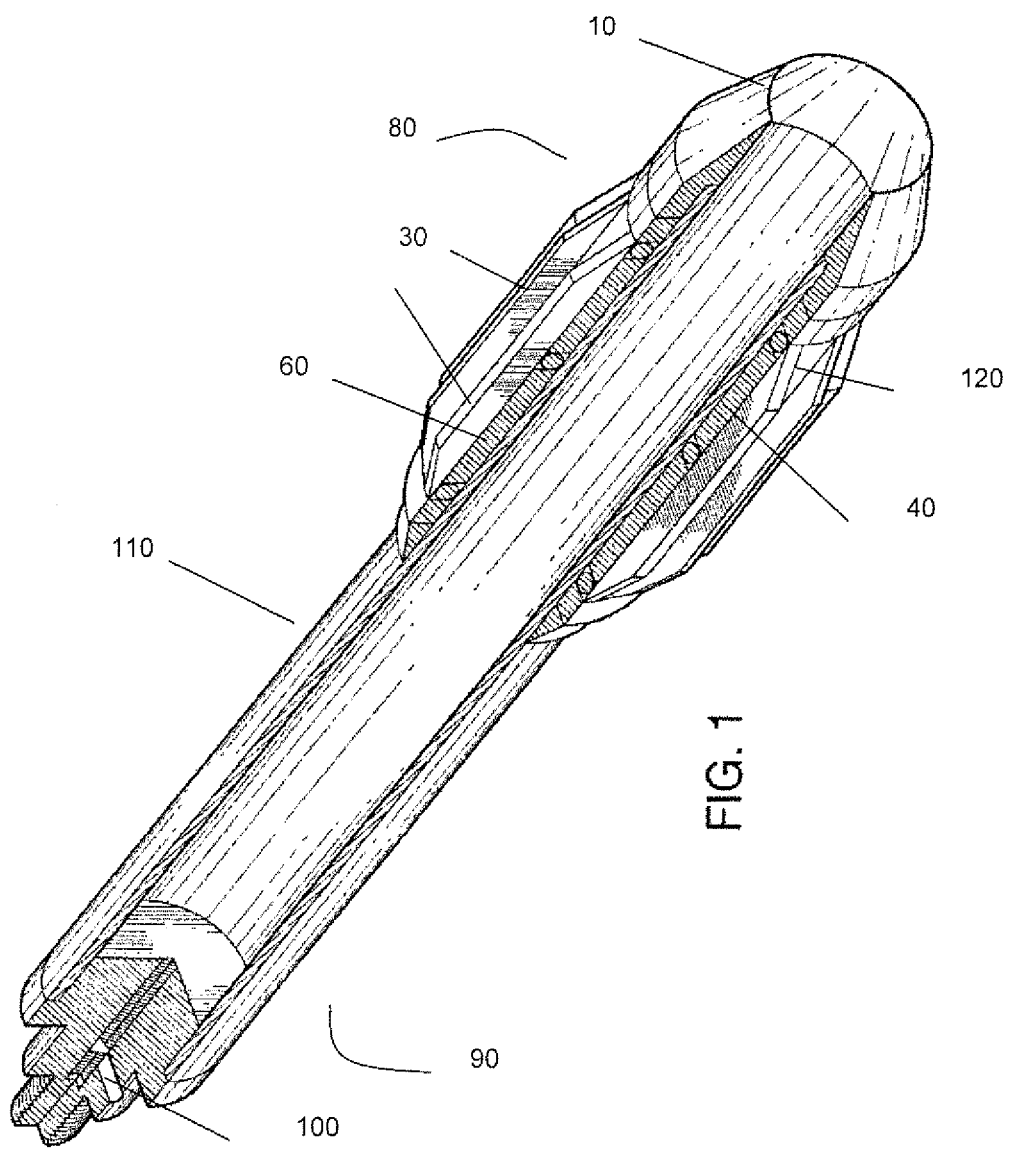
FIG. 1 is a perspective view of a groundwater sampling tool according to one non-limiting embodiment of the disclosed subject matter.

One aspect of the presently disclosed subject matter provides a groundwater sampling tool that includes an elongated hollow coring tube having a proximal end and a distal end for collecting groundwater and sediment, and a Peltier element located in close proximity to a wall of the elongated hollow coring tube adapted to freeze groundwater and sediment collected by the elongated hollow coring tube.

In certain non-limiting embodiments, the ground water sampling tool can further include a cutting tip engaged to the distal end of the elongated hollow coring tube. The cutting tip can be composed of, for example, a high alloy steel. The distal end of the elongated tube can be threaded and the cutting tip can be adapted to screw on the distal end of the elongated tube.

In one embodiment, the groundwater sampling tool can further include a layer of insulation in close proximity to the Peltier element, such as a layer of an epoxy fiberglass composite. O-rings can interspace the Peltier element and the layer of insulation to provide shock insulation.

The groundwater sampling tool can also further include heat transfer and support fins that can be located, for example, on the outside of the elongated hollow coring tube and encapsulating the Peltier element. A heat pipe in communication with the Peltier element adapted to carry heat upward and away from the groundwater and sediment collected by the elongated hollow coring tube can also be provided. Further, the proximal end of the elongated hollow coring tube can include an air vent.

In one embodiment, the Peltier element is contained within a housing capable of receiving current applied to the elongated hollow coring tube. The housing can contain an oil or other medium to aid in heat transfer.

A power source can also be provided, and the power source can be adapted to apply power to the elongated hollow coring tube. In one non-limiting embodiment, the power source is a car battery.

Another aspect of the presently disclosed subject matter provides a method of obtaining a groundwater sample that includes providing a groundwater sampling tool that includes an elongated hollow coring tube having a proximal end and a distal end for collecting groundwater and sediment, a Peltier element located in close proximity to a wall of the elongated hollow coring tube adapted to freeze groundwater and sediment contained within the elongated hollow coring tube, introducing the groundwater sampling tool to a subterranean source of groundwater and sediment, applying power from a power source to the elongated hollow coring tube for a time sufficient to freeze the sample of groundwater contained therein, and removing the groundwater sampling tool with the frozen sample of groundwater contained therein from the subterranean source of groundwater and sediment.

In one embodiment, the power source is a car battery. The power source can, in one embodiment, provide less than 45 volts.

While any method can be employed to introduce to groundwater sampling tool to the subterranean source of groundwater and sediment, hand-driven force is used in one non-limiting embodiment (e.g., introduced via hand-hammering).

As used herein, a "Peltier element" or "Peltier cooler" refers to any device that, upon the application electrical power, provides cooling based the heat flux between the junction of two different types of materials, generally known as the Peltier effect.

For example, a Peltier element can be a series of diode junctions (e.g., PN junctions) arranged symmetrically between two electrically-insulating plates. Depending on which direction the current passes through the series circuit of diode junctions, the charge carrier pairs will be swept from one side, which will experience cooling, to the other side where they are recombined and release the bandgap energy as heat. As known to the those of ordinary skill in the art, Peltier elements are provided by numerous manufacturers and distributors in various geometries and power ranges.

Values provided below with respect to non-limiting Peltier coolers are for purposes of illustration and not limitation. About 10 kJ of cooling can be required to freeze a block of sediment having a diameter of 37 mm and a height of 37 mm, assuming that sand accounts for about 60 to 80% of the volume. With a $\Delta T$ of zero, the input power (and resulting waste heat) can be about 2 times the wattage of heat removed. To provide 1 watt of cooling, 3 watts of heat are dissipated. Using three 54 watt Peltier elements (rated in terms of input power), each of which can move 27 watts where the temperature difference is zero, one can estimate that the time to freeze the sample block of 37 mm (diameter)×37 mm (height) will be less than 6 minutes, taking into account the drop in efficiency of Peltier coolers as $\Delta T$ increases.

FIG. 1 provides a perspective view of a groundwater sampling tool according to one non-limiting embodiment of the disclosed subject matter. The distal end of the device (80) is provided with a threaded cap, and the proximal end of the device (90) is provided with an air vent (100). A section of the coring tube (110) can be turned down to make space for the Peltier cooler. The tip can be replaced with a screw-on cutting tip (10) made of, for example, high alloy steel that can hold the system together. Also shown in FIG. 1, a set of heat transfer fins (30) can be provided. The fins should not hamper penetration into the sediment, but will impart strength to a cover shell (120) that protects the Peltier element (40) and a thermal insulation sleeve (60).

Figure 2:
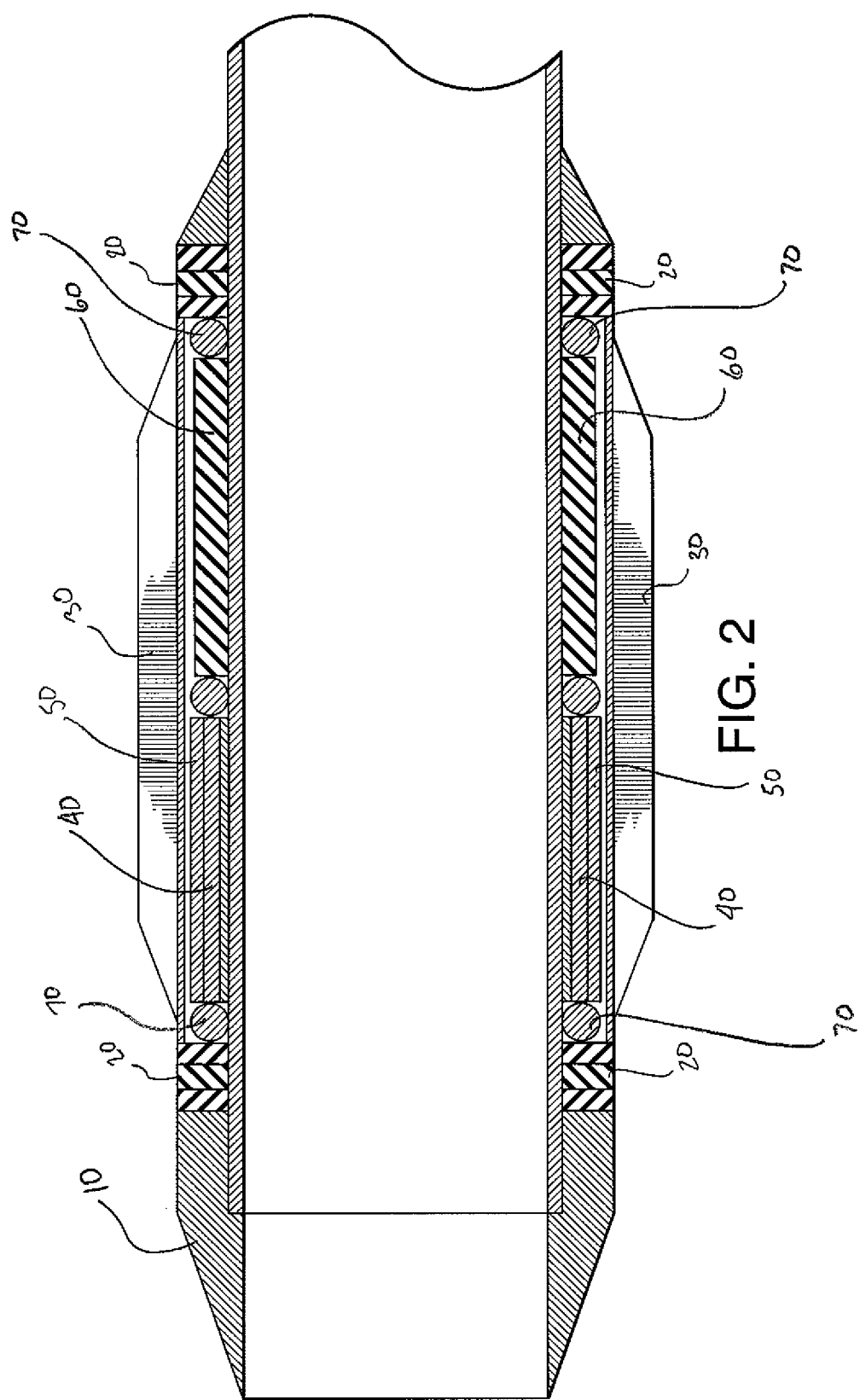
FIG. 2 is a cross-section view of the groundwater sampling tool also depicted in FIG. 1.

These features are also shown in FIG. 2, which provides a cross-section of the illustrative embodiment also shown in FIG. 1. A high strength threaded cutting tip (10) is provided at the distal end of the device. The cutting tip can compress insulated retaining rings (20) at both right (top) and left (bottom) of the heat transfer and support fins (30). Peltier cooling elements (40) and Peltier housing (50) is provided near the distal end of the groundwater sampling tool. An epoxy-fiberglass composite sleeve or insulation ring (60) is provided to insulate the (lower, inside) cool side from the (upper, outside) hot side of the tube. O-rings (70) can be interspaced throughout to provide shock isolation. The inner section can be filled with oil to aid heat transfer.

Commercially available, off the shelf Peltier elements are available in flat packages. To fit the Peltier elements to the cylinder, a prismatic ring of metal (e.g., brass) with flat faces can be machined. The Peltier devices can be epoxied to the prismatic ring. Electric contact can be made, for example, with beryllium-copper spring sheets. The ring of Peltier elements can be free to slide up and down the body of the sampling tool for decoupling from vertical shock.

In this embodiment, the body of the device can carry current to the inner face of the Peltier housing, while the protective cover (with heat transfer and support fins) can carry current away through the upper retaining ring. According to an alternative embodiment, the sampling tool can be provided with a heat pipe in addition to, or in place of, the heat transfer and support fins to direct heat generated by the Peltier element upward and away from the sample of groundwater and sediment contained within the elongated hollow coring tube.

A car battery can be used to power the sampling tool in the field. For a number 12 copper wire (~2 mm in diameter), the voltage drop to a depth of 30 meters is only about 1.45 volts at 10 amps, which can be expressed as a 10% efficiency loss, for a circuit operating on 18 volts at 10 amps. The return current can be carried by the steel drive rods. This power level can correspond to three 6-volt, 10-ampere Peltier coolers wired in series. Other combination are possible, such as higher voltages, but below the lethal 45 volt threshold.

In addition to the specific embodiments described above and claimed below, the disclosed subject matter is also directed to other embodiments having any other possible combination of the features disclosed above. As such, the particular features disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A groundwater sampling tool comprising:
    (a) an elongated hollow coring tube having a proximal end and a distal end for collecting groundwater and sediment; and
    (b) a Peltier element located in close proximity to a wall of the elongated hollow coring tube adapted to freeze groundwater and sediment collected by the elongated hollow coring tube,
    wherein the Peltier element is contained within a housing, and wherein the Peltier element is powered by electrical current applied to the housing via the hollow coring tube.

2. The groundwater sampling tool of claim 1, further comprising heat transfer and support fins located on the outside of the elongated hollow coring tube and encapsulating the Peltier element.

3. The groundwater sampling tool of claim 1, wherein the housing contains an oil to aid in heat transfer.

4. The groundwater sampling tool of claim 1, wherein the proximal end of the elongated hollow coring tube comprises an air vent.

5. The ground water sampling tool of claim 1, further comprising a cutting tip engaged to the distal end of the elongated hollow coring tube.

6. The groundwater sampling tool of claim 5, wherein the distal end of the elongated tube is threaded and the cutting tip is adapted to screw on the distal end of the elongated tube.

7. The groundwater sampling tool of claim 5, wherein the cutting tip is composed of a high alloy steel.

8. The groundwater sampling tool of claim 1, further comprising a layer of insulation substantially proximally adjacent to the Peltier element.

9. The groundwater sampling tool of claim 8, wherein the layer of insulation includes an epoxy fiberglass composite.

10. The groundwater sampling tool of claim 8, wherein at least one o-ring interspaces the Peltier element and the layer of insulation.

11. The groundwater sampling tool of claim 1, further comprising a power source adapted to apply power to the elongated hollow coring tube.

12. The groundwater sampling tool of claim 11, wherein the power source is a car battery.

13. A method of obtaining a groundwater sample, comprising:
    (a) providing a groundwater sampling tool that includes
        (i) an elongated hollow coring tube having a proximal end and a distal end for collecting groundwater and sediment; and
        (ii) a Peltier element located in close proximity to a wall of the elongated hollow coring tube adapted to freeze groundwater and sediment contained within the elongated hollow coring tube, wherein the Peltier element is contained within a housing, and wherein the Peltier element is powered by electrical current applied to the housing via the hollow coring tube;
    (b) introducing the groundwater sampling tool to a subterranean source of groundwater and sediment;
    (c) applying power from a power source to the elongated hollow coring tube for a time sufficient to freeze the sample of groundwater contained therein; and
    (d) removing the groundwater sampling tool with the frozen sample of groundwater contained therein from the subterranean source of groundwater and sediment.

14. The method of obtaining a groundwater sample of claim 13, wherein the groundwater sampling tool further comprises a cutting tip engaged to the distal end of the elongated hollow coring tube.

15. The method of obtaining a groundwater sample of claim 13, wherein the groundwater sampling tool further comprises a heat pipe in communication with the Peltier element adapted to carry heat upward and away from the groundwater and sediment collected by the elongated hollow coring tube.

16. The method of obtaining a groundwater sample of claim 13, wherein the power source is a car battery.

17. The method of obtaining a groundwater sample of claim 13, wherein the power from the power source is less than 45 volts.

18. The method of obtaining a groundwater sample of claim 13, wherein the groundwater sampling tool is introduced to the subterranean source of groundwater and sediment by hand-driven force.

\* \* \* \* \*